(12) United States Patent
Cheung et al.

(10) Patent No.: US 6,642,197 B1
(45) Date of Patent: Nov. 4, 2003

(54) GERMICIDAL BLOOMING TYPE COMPOSITIONS CONTAINING BIPHENYL SOLVENTS

(75) Inventors: Tak Wai Cheung, Bridgewater, NJ (US); Dennis Thomas Smialowicz, West Milford, NJ (US)

(73) Assignee: Reckitt Benckiser Inc., Wayne, NJ (US)

( * ) Notice: Subject to any disclaimer, the term of this patent is extended or adjusted under 35 U.S.C. 154(b) by 0 days.

(21) Appl. No.: 09/890,031

(22) PCT Filed: Jan. 24, 2000

(86) PCT No.: PCT/GB00/00188

§ 371 (c)(1),
(2), (4) Date: Nov. 9, 2001

(87) PCT Pub. No.: WO00/44868

PCT Pub. Date: Aug. 3, 2000

(30) Foreign Application Priority Data

Jan. 27, 1999 (GB) ............................................... 9901702

(51) Int. Cl.[7] .............................. C11D 3/50; C11D 3/26; C11D 7/50

(52) U.S. Cl. .................. 510/407; 510/101; 510/238; 510/239; 510/240; 510/384; 510/433; 510/434; 510/477; 510/503

(58) Field of Search ................................. 510/407, 101, 510/238, 239, 240, 384, 433, 434, 877, 503; 134/42

(56) References Cited

U.S. PATENT DOCUMENTS 5,773,398 A 6/1998 Joye et al.
6,184,195 B1 * 2/2002 Cheung et al.

FOREIGN PATENT DOCUMENTS

| JP | 2-150497 | 6/1990 |
| JP | 6220493 | 8/1994 |
| WO | WO 97/06230 | 2/1997 |

* cited by examiner

Primary Examiner—Gregory E. Webb
(74) Attorney, Agent, or Firm—Fish & Richardson P.C.

(57) ABSTRACT

Aqueous concentrated liquid hard surface cleaning compositions, which bloom when added to a larger volume of water, comprise: an organic solvent constituent; a germicidal constituent which provides a primary sanitizing benefit, preferably a quaternary ammonium compound; a binary co-solvent system comprising an alkyl diphenyl solvent and at least one co-solvent; optionally, a further detersive surfactant constituent; optionally, but desirably, at least one constituent selected from chelating agents, coloring agent, light stabilizers, fragrances, thickening agents, hydrotropes, pH adjusting agents and pH buffers.

30 Claims, No Drawings

GERMICIDAL BLOOMING TYPE COMPOSITIONS CONTAINING BIPHENYL SOLVENTS

BACKGROUND OF THE INVENTION

The present invention relates to blooming type hard surface cleaning and disinfecting compositions. More particularly the present invention relates to concentrated liquid cleaning and disinfecting compositions which are normally diluted in a larger volume of water to form a working solution therefrom, and which exhibit a blooming effect when diluted.

Blooming is a property exhibited by dilutable compositions such as known cleaning compositions, specifically pine-oil type cleaning compositions which contain a significant amount (generally at least about 5% and more) of pine oil. Certain other known-art formulations, such as LYSOL (RTM) (where "RTM" indicates a proprietary tradename, or trademark) disinfectant concentrate (Reckitt & Colman, Inc., Montvale N.J. also exhibit such a blooming property. Blooming may be characterized as formation of milky, creamy or cloudy appearance which is manifested when a dilutable composition is added to a larger volume or quantity of water. Such blooming is particularly desirable in compositions where the blooming characteristic in an aqueous dilution is long lasting.

SUMMARY OF THE INVENTION

Accordingly it is an object of the invention to provide an aqueous concentrated liquid hard surface cleaning composition which blooms when added to a larger volume of water which comprises the following constituents:

an organic solvent constituent;

a germicidal constituent which provides a primary sanitizing benefit, preferably a quaternary ammonium compound;

binary co-solvent system comprising an alkyl diphenyl solvent and at least one co-solvent;

optionally, a further detersive surfactant constituent;

optionally but desirably at least one optional constituent selected from: chelating agents, coloring agent, light stabilizers, fragrances, thickening agents, hydrotropes, pH adjusting agents, pH buffers, as well as others known the art and useful in similar compositions. The one or more optional constituents are selected to be present, and are included in amounts which do not undesirably affect the overall blooming characteristics of the present inventive compositions.

In preferred embodiments the concentrate compositions provide excellent initial blooming characteristics in 'as mixed' dilutions with water, but also exhibit good retention of blooming characteristics over a longer time period, viz., days and weeks.

A further aspect of the invention is a concentrated liquid hard surface cleaning composition wherein the composition exhibits a blooming effect when diluted in a larger volume of water.

DETAILED DISCLOSURE

Desirably, the inventive compositions are essentially free of terpene solvents such as alpha-terpineols or d-Limonene which are characteristic of products such as so-called "pine oil" cleaning compositions which typically include such terpene solvents.

The inventive compositions include an organic solvent constituent. Many useful organic solvents may be used, as long as it does not undesirably disrupt the favorable characteristics of the invention, especially the blooming characteristic. Mixtures of two or more organic solvents may also be used as the organic solvent constituent.

Useful organic solvents are those which are at least partially water-miscible organic solvents such as alcohols, water-miscible ethers (e.g. diethylene glycol diethylether, diethylene glycol dimethylether, propylene glycol dimethylether), water-miscible glycol ethers (e.g. propylene glycol monomethylether, propylene glycol mono ethylether, propylene glycol monopropylether, propylene glycol monobutylether, ethylene glycol monobutylether, dipropylene glycol monomethylether, diethyleneglycol monobutylether), lower esters of monoalkylethers of ethylene glycols or propylene glycols (e.g. propylene glycol monomethyl ether acetate) all commercially available from Union Carbide, Dow Chemicals or Höchst. Mixtures of organic solvents can also be used.

Particularly useful organic solvents include glycols such as alkylene glycols such as propylene glycol, and glycol ethers. Examples of such glycol ethers include those having the general structure $R_a$—O—$R_b$—OH, wherein $R_a$ is an alkyl of 1 to 20 carbon atoms, or an aryl of at least 6 carbon atoms, and $R_b$ is an alkylene of 1 to 8 carbons or is an ether or polyether containing from 2 to 20 carbon atoms. Examples of such useful glycol ethers include propylene glycol methyl ether, dipropylene glycol methyl ether, tripropylene glycol methyl ether, propylene glycol isobutyl ether, ethylene glycol methyl ether, ethylene glycol ethyl ether, ethylene glycol butyl ether, diethylene glycol phenyl ether, propylene glycol phenol ether, and mixtures thereof. Preferred are ethylene glycol n-butyl ether, diethylene glycol n-butyl ether, and mixtures thereof. Such glycol ethers are presently commercially available from a number of sources including in the DOWANOL™ glycol ether from The Dow Chemical Company, Midland Mich. (USA).

Further particularly useful organic solvents monohydric (straight chained or branched) primary, secondary or tertiary lower aliphatic alcohols, especially $C_1$–$C_6$ aliphatic primary and secondary alcohols, of which isopropanol is particularly preferred. The present inventors have found that inclusion of the organic solvent constituent in amounts of about 0.001% by weight to about 50% by weight have been found to be effective in providing effective cleaning, particularly when the compositions are dispersed into a larger volume of water, as well as in solubilizing other less water soluble constituents present in the concentrate compositions of the invention. Preferably, the organic solvent constituent is present in amounts of from 0.1–40% by weight, and most preferably from about 0.1–35% by weight.

Additionally the inventor has found the according to certain preferred embodiments the organic solvent constituent, comprises, and in certain especially preferred embodiments consist essentially of, both an alkylene glycol such as propylene glycol, and a monohydric lower aliphatic alcohol such as a $C_1$–$C_6$ aliphatic primary and secondary alcohol, especially isopropyl alcohol.

The inventive compositions also include a germicidal constituent which provides a primary sanitizing benefit, preferably a quaternary ammonium compound;

The compositions of the invention include a disinfecting effective amount of a quaternary ammonium compound having germicidal properties. Particularly useful quaternary ammonium compounds and salts thereof include quaternary ammonium germicides which may be characterized by the general structural formula:

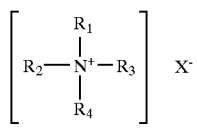

where at least one of $R_1$, $R_2$, $R_3$ and R4 is a hydrophobic, aliphatic, aryl aliphatic or aliphatic aryl radical of from 6 to 26 carbon atoms, and the entire cation portion of the molecule has a molecular weight of at least 165. The hydrophobic radicals may be long-chain alkyl, long-chain alkoxy aryl, long-chain alkyl aryl, halogen-substituted long-chain alkyl aryl, long-chain alkyl phenoxy alkyl, aryl alkyl, etc. The remaining radicals on the nitrogen atoms other than the hydrophobic radicals are substituents of a hydrocarbon structure usually containing a total of no more than 12 carbon atoms. The radicals $R_1$, $R_2$, $R_3$ and $R_4$ may be straight chained or may be branched, but are preferably straight chained, and may include one or more amide or ester linkages. The radical X may be any salt-forming anionic radical.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide or ester linkages such as octyl phenoxy ethoxy ethyl dimethyl benzyl ammonium chloride, N-(laurylcocoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

Preferred quaternary ammonium compounds which act as germicides and which are found useful in the practice of the present invention include those which have the structural formula:

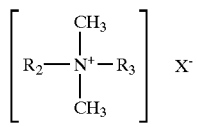

wherein $R_2$ and $R_3$ are the same or different $C_8$–$C_{12}$ alkyl, or $R_2$ is $C_{12-16}$ alkyl, $C_{8-18}$ alkylethoxy, $C_{8-18}$ alkylphenolethoxy and $R_3$ is benzyl, and X is a halide, for example chloride, bromide or iodide, or X may be methosulfate, or a saccharide. The alkyl groups recited in $R_2$ and $R_3$ may be straight chained or branched, but are preferably substantially linear.

Particularly useful quaternary germicides include compositions which include a single quaternary, as well as mixtures of two or more different quaternaries. Particularly useful quaternary germicides include alkyl dimethyl benzyl ammonium chlorides, including those based on dialkyl($C_8$–$C_{10}$) dimethyl ammonium chlorides; as well as didecyl dimethyl ammonium chlorides, dioctyl dimethyl ammonium chlorides, alkyl dimethyl benzyl ammonium chlorides, alkyl dimethyl ethyl benzyl ammonium chlorides, myristyl dimethyl benzyl ammonium chlorides, methyl dodecyl xylene-bis-trimethyl ammonium chlorides, benzethonium chlorides, alkyl dimethyl benzyl ammonium chlorides, including mixtures of one or more of the above. These materials are available as BARDAC (RTM), BARQUAT (RTM), BTC (RTM), LONZABAC (RTM), as well as other tradenames (ex. Stepan Co., or Lonza AG). These quaternary ammonium compounds are desirably present in the concentrate compositions in an amount of from about 0.001–5% wt., are desirably present in an amount of from 0.1–3% wt. and most desirably are present in an amount of from 0.5–3% wt. When diluted in a larger volume of water to form a cleaning and disinfecting composition, the quaternary ammonium compounds should be present in sufficient amount such that they are in a concentration of at least about 250 parts per million (p.p.m.), more desirably at least about 450 p.p.m. and most desirably at least about 600 p.p.m.

The inventive compositions further also include a binary co-solvent system comprising alkyl diphenyl solvent and a co-solvent which aids in the solubilization of the diphenyl solvent in an aqueous medium.

The alkyl diphenyl solvent is one which may be generally represented by the formula

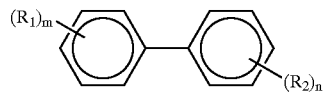

wherein:
$R_1$ is hydrogen or is a lower alkyl radical, preferably a $C_1$–$C_{10}$, but more preferably is a $C_1$–$C_6$ straight chained or branched alkyl radical,
$R_2$ is a lower alkyl radical, preferably a $C_1$–$C_{10}$, but more preferably is a $C_1$–$C_6$ straight chained or branched alkyl radical,
m is an integer from 1–3 inclusive; and,
n is an integer from 1–3 inclusive.
Preferably $R_1$ is any one of the values indicated above, m is 1, and $R_2$ has any of the values indicated above. More preferably, $R_1$ is a $C_1$–$C_6$ straight chained or branched alkyl radical and m is 1, and $R_2$ is a $C_1$–$C_6$ straight chained or branched alkyl radical. It is to be understood that mixtures of the compounds indicated above may be used as the diphenyl solvent constituent.

Such alkyl diphenyls are, per se, known to the art, and are described in U.S. Pat. No. 3,787,181. Particularly useful as the alkyl diphenyl solvent are materials presently marketed as NUSOLV(RTM) ABP solvents available from Arristec, Inc. (Easton, Pa.) described to be a high purity alkyl diphenyls and mixtures thereof, and is also available from Koch Chemical Co. (Corpus Christi, Tex.) as SURESOL (RTM) solvents.

The alkyl diphenyl solvent may be present in the concentrate compositions in amounts of from about 0.001% by weight to up to about 20% by weight, preferably about 0.01–10% by weight, most preferably in amount of between 0.1–8% by weight.

The inventors have observed that the concentrated compositions of the invention are greatly improved with the addition of a co-solvent. This co-solvent aids in the solubilization of the alkyl diphenyl solvent in water is desirably an at least partially water-miscible monohychic primary alcohol, especially a water-miscible monohydric primary $C_8$–$C_{18}$ alcohol. Particularly effective are cetyl, lauryl and myristyl alcohols, especially lauryl alcohols. Mixtures of such solvents are also contemplated as being useful as the co-solvent. The inventors have found that the inclusion of such alcohols greatly aids in the dissolution of the alkyl diphenyl solvents in the concentrate compositions according to the invention being described herein, which aids in ensuring that clarity of the concentrate composition is maintained which is particularly desirable from a consumer standpoint.

The co-solvent may be present in the concentrate compositions in amounts of from about 0.001% by weight to up to about 5% by weight, preferably about 0.01–3% by weight, most preferably in amount of between 0.1–2% by weight.

Water is added in order to provide 100% by weight of the concentrate composition. Water is added in amounts which are sufficient to form the concentrated compositions which amount is sufficient to ensure the retention of a substantially clear characteristic when produced as a concentrate, but at the same time ensuring good blooming upon the addition of the concentrated composition to a further amount of water, or upon the addition of further water to the concentrate. The water may be tap water, but is preferably distilled and/or deionized water.

Other conventional additives known to the art but not expressly enumerated here may also be included in the compositions according to the invention. By way of non-limiting example without limitation these may include: chelating agents, coloring agents, light stabilizers, fragrances, thickening agents, hydrotropes, pH adjusting agents, pH buffers as well as one or more detersive surfactants which do not deleteriously detract from the blooming characteristics of the inventive compositions. Many of these materials are known to the art, per se, and are described in *McCutcheon's Detergents and Emulsifiers*, North American Edition, 1982; *Kirk-Othmer, Encyclopedia of Chemical Technology*, 3rd Ed., Vol. 22, pp. 346–387, the contents of which are herein incorporated by reference. Mixtures of two or more such surface active agents may be incorporated into the inventive compositions. Such optional, i.e., non-essential constituents should be selected so to have little or no detrimental effect upon the desirable characteristics of the present invention, namely the blooming behavior, cleaning efficacy, hard surface cleaning activity, and low toxicity as provided by the inventive compositions. Generally the total weight of such further conventional additives may comprise up to 20% by weight of a concentrated composition formulation.

Exemplary useful buffers include the alkali metal phosphates, polyphospates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use buffers such materials as aluminosilicates (zeolites), borates, aluminates and certain organic materials such as gluconates, succinates, maleates, and their alkali metal salts. Such buffers keep the pH ranges of the compositions of the present invention within acceptable limits.

When a fragrance is included in a concentrate composition being taught herein, the amount of such a fragrance is generally not in excess of 0.5% wt., but is preferably even less, i.e., to 0.20% wt, but generally even less, i.e., to 0.1 0% wt. It is contemplated that this fragrance constituent may include among its active agents terpene oils (alpha-terpenol, d-Limonene) which is included to provide a fragrance characteristic of a pine oil containing constituent. It is understood that such may be present in the inventive compositions as they may form part of the fragrance constituent forming part of a concentrate composition. However, it is noted that the inventive compositions will function and exhibit satisfactory blooming effect without such a fragrance constituent being present, i.e., if it is omitted. Compositions which include such fragrances are considered to be 'essentially free' of terpene solvents.

Exemplary useful pH adjusting agents include known materials such as inorganic acids, (e.g., hydrochloric), organic acids (e.g., citric, glycolic) or inorganic bases may be used to adjust the pH of the concentrate compositions to a desired range.

The inventive compositions further include optionally, but in certain embodiments, desirably, one or more further detersive surfactants. Useful detersive surfactants include anionic, nonionic, cationic and amphoteric surfactants which are found to not undesirably detract from the blooming characteristics of the present invention.

The useful nonionic surfactants, include known art nonionic surfactant compounds. Practically any hydrophobic compound having a carboxy, hydroxy, amido, or amino group with a free hydrogen attached to the nitrogen can be condensed with ethylene oxide or with the polyhydration product thereof, polyethylene glycol, to form a water soluble nonionic surfactant compound. Further, the length of the polyethylenoxy hydrophobic and hydrophilic elements may various. Exemplary nonionic compounds include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides. Exemplary preferred nonionic surfactants are ethoxylated higher aliphatic, primary alcohols presently commercially available under the trade name NEODOL (RTM) (ex., Shell Chemical Co., Houston, Tex. (USA)), which as well as the condensation products of a secondary aliphatic alcohols containing 8 to 18 carbon atoms in a straight or branched chain configuration condensed with 5 to 30 moles of ethylene oxide, including those presently commercially available under the trade name of TERGITOL (RTM) (ex, Union Carbide Co., Danbury, Conn. (USA)).

Other suitable nonionic surfactant compositions include the polyethylene oxide condensates of one mole of alkyl phenol containing from about 8 to 18 carbon atoms in a straight- or branched chain alkyl group with about 5 to 30 moles of ethylene oxide, including those which are presently commercially available under the trade name of IGEPAL (RTM) (ex., Rhône-Poulenc, Princeton N.J.(USA)). Further useful nonionic surfactants include the water-soluble condensation products of a $C_8$–$C_{20}$ alkanol with a mixture of ethylene oxide and propylene oxide wherein the weight ratio or ethylene oxide to propylene oxide is from 2.5:1 to 4:1, preferably 2.89:1 to 3.3:1, with the total of the ethylene oxide; and propylene oxide (including the terminal ethanol or propanol group) being from 60–85%, preferably 70 to 80%, by weight. Such include those commercially available under the trade name of PLURAFAC (RTM) (ex., BASF Corp., Hackettstown, N.J. (USA)). Still further useful water-soluble nonionic surfactants include condensation products of a $C_8$–$C_{20}$ alkanols with a mixture of ethylene oxide and/or propylene oxide. Such are commercially available under the tradename POLYTERGENT (RTM) (ex., Olin Chemical Co., Stamford Conn.(USA)).

Further suitable water-soluble nonionic surfactants which may also be used include those which are marketed under the trade name PLURONIC (RTM) (ex., BASF Corp., Hackettstown, N.J. (USA)). These are formed by condensing ethylene oxide with a hydrophobic base formed by the condensation of propylene oxide with propylene glycol. Further useful nonionic surfactants include alkylmonoglycosides and alkylpolyglycosides which are alkaline and electrolyte stable. Various glycoside and polyglycoside compounds including alkoxylated glycosides may be used. Examples of such alkylglycosides as described above include, for example, APG™ 325 CS GLYCOSIDE which is described as being a 50% $C_9$–$C_{11}$ alkyl polyglycoside, also commonly referred to as D-glucopyranoside, (commercially available from Henkel Corp, Ambler Pa.) and GLUCOPON (RTM) 625 CS which is described as being a 50% $C_{10}$–$C_{16}$ alkyl polyglycoside, also commonly referred to as a D-glucopyranoside, (available from Henkel Corp., Ambler Pa.).

One class of particularly useful detersive surfactants are polymeric alkylene oxide block copolymer. Polymeric alkylene oxide block copolymers include nonionic surfactants in which the major portion of the molecule is made up of block polymeric $C_2$–$C_4$ alkylene oxides. Such nonionic surfactants, while preferably built up from an alkylene oxide chain starting group, and can have as a starting nucleus almost any active hydrogen containing group including, without limitation, amides, phenols, thiols and secondary alcohols.

One group of such useful nonionic surfactants containing the characteristic alkylene oxide blocks are those which may be generally represented by the formula (A):

$$HO\text{---}(EO)_x(PO)_y(EO)_z\text{---}H \quad (A)$$

where

EO represents ethylene oxide,

PO represents propylene oxide, y equals at least 15, $(EO)_{x+z}$ equals 20 to 50% of the total weight of said compounds, and, the total molecular weight is preferably in the range of about 2000 to 15,000.

Further exemplary useful nonionic surfactants which may be used include certain alkanolamides including monoethanolamides and diethanolamides, particularly fatty monoalkanolamides and fatty dialkanolamides. Commercially available monoethanol amides and diethanol amides include those marketed under the trade names ALKAMIDE (RTM) and CYCLOMIDE (RTM) by Rhône-Poulenc Co., (Cranbury, N.J.).

The nonionic surfactants, when present, can be present either singly, or as a mixture of two or more nonionic surfactant compounds as defined above.

The concentrate compositions may also include one or more amine oxide surfactant constituents. Such amine oxides frequently desirably improve the miscibility of the pine oil constituents in the aqueous phase of the concentrate compositions. Non-limiting examples of useful amine oxide semi-polar nonionic surfactants include those according to the formulae:

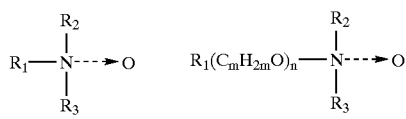

wherein $R_1$ is hydrogen or is an alkyl, 2-hydroxyalkyl, 3-hydroxyalkyl, or 3-alkoxy-2-hydroxypropyl radical where the alkyl and alkoxy parts contain from about 8 to about 18 carbon atoms, $R_2$ and $R_3$ are independently selected from methyl, ethyl, propyl, isopropyl, 2-hydroxyethyl, 2-hydroxypropyl, or 3-hydroxypropyl, m is an integer from 2 to 4, and n is an integer from 0 to about 10. Preferably, the amine oxide semi-polar nonionic surfactants are those according to the formula immediately preceding wherein $R_1$ is an alkyl radical of from 12 to 16 carbon atoms, $R_2$ and $R_3$ are independently selected from methyl or ethyl, m is 2, and n is 0. Specific examples of such useful amine oxide semi-polar nonionic surfactants include cetyl-, myristyl- or lauryl-dimethyl amine oxide or mixtures thereof.

A further useful general class of useful amine oxides which may be included in the amine oxide constituent according to the invention are further alkyl di (lower alkyl) amine oxides in which the alkyl group has about 10–20, and preferably 12–16 carbon atoms, and can be straight or branched chain, saturated or unsaturated. The lower alkyl groups include between 1 and 7 carbon atoms. Examples include those described above, as well as those in which the alkyl group is a mixture of different amine oxides, dimethyl cocoamine oxides, dimethyl (hydrogenated tallow) amine oxides, and myristyl/palmityl dimethyl amine oxides.

A further class of useful amine oxides include alkyl di (hydroxy lower alkyl) amine oxides in which the alkyl group has about 10–20, and preferably 12–16 carbon atoms, and can be straight or branched chain, saturated or unsaturated. Examples are bis(2-hydroxyethyl) cocoamine oxide, bis(2-hydroxyethyl) tallowamine oxide; and bis(2-hydroxyethyl) stearylamine oxide.

Further useful amine oxides include those which may be characterized as alkylamidopropyl di(lower alkyl) amine oxides in which the alkyl group has about 10–20, and preferably 12–16 carbon atoms, and can be straight or branched chain, saturated or unsaturated. Examples are cocoamidopropyl dimethyl amine oxide and tallowamidopropyl dimethyl amine oxide; and Additional useful amine oxides include those which may be referred to as alkylmorpholine oxides in which the alkyl group has about 10–20, and preferably 12–16 carbon atoms, and can be straight or branched chain, saturated or unsaturated.

Exemplary amine oxide surfactant constituents include AO-728 (RTM)which is described to be a composition containing 50% wt. of bis-(2-hydroxyethyl $C_2$–$C_{15}$ alkyloxypropyl) amine oxide (ex. Tomah Products Inc., Milton Wis.), and AMMONYX(RTM) CDO Special described to be cocoamidopropyl dimethyl amine (Stepan Co., Northfield Ill.).

Exemplary anionic surfactants include compounds known to the art as useful as anionic surfactants. These include but are not limited to: alkali metal salts, ammonium salts, amine salts, aminoalcohol salts or the magnesium salts of one or more of the following compounds: alkyl sulfates, alkyl ether sulfates, alkylamidoether sulfates, alkylaryl polyether sulfates, monoglyceride sulfates, alkylsulfonates, alkylamide sulfonates, alkylarylsulfonates, olefinsulfonates, paraffin sulfonates, alkyl sulfosuccinates, alkyl ether sulfosuccinates, alkylamide sulfosuccinates, alkyl sulfosuccinamate, alkyl sulfoacetates, alkyl phosphates, alkyl ether phosphates, acyl sarcosinates, acyl isethionates, and N-acyl taurates. Generally, the alkyl or acyl radical in these various compounds comprise a carbon chain containing 12 to 20 carbon atoms.

Further exemplary anionic surface active agents which may be used include fatty acid salts, including salts of oleic, ricinoleic, palmitic, and stearic acids; copra oils or hydrogenated copra oil acid, and acyl lactylates whose acyl radical contains 8 to 20 carbon atoms.

Further exemplary and preferred anionic surface active agents include alkyl carboxylates, and especially alkyl ether carboxylates, particularly those having the general structural formula:

$$R-O-(C_nH_{2n}O)_m-R_1-COO^-M^+$$

wherein R is a straight or branched, long chain, alkyl group containing from 8 to 18 carbon atoms, n is an integer from 2 to 4, m is an integer from 1 to 100, $R_1$ is $CH_2$, $CH_2CH_2$, or $CH_2CH_2CH_2$, and M is a counterion such as an organic or inorganic cation including singly valent cations as well as polyvalent cations. Exemplary cations include cations of an alkali metal including sodium or lithium, or organic cations such as ammonium, diethylammonium, or triethylammonium cations, as well as other cations not particulary recited here. Such anionic alkyl ether carboxylates are known to be useful as surfactant compositions. In the compositions according to the instant invention, preferably n is 2, m is 4–11, R is $C_9$–$C_{16}$, $R_1$ is $CH_2$ and M is the cation of an alkali metal, preferably sodium. Such surfactants are presently commercially available under the trade name SANDOPAN (RTM) (Clariant Chemical Corp., Charlotte N.C.), NEODOX (RTM) 25-6 and NEODOX (RTM) 23-4 (Shell Chemical Co., Houston, Tex.), as well as SURFINE (RTM) WLG(Finetex Inc., Elmwood Park, N.J.).

Exemplary amphoteric surface active agents include, by way of non-limiting example, one or more further known art surfactant compositions, including betaines, ethylene oxide condensates, and fatty acid amides.

Exemplary useful betaine surfactants include those according to the general formula:

$$R-N^+(R_1)_2-R_2C^-OO$$

wherein R is a hydrophobic group selected from the group consisting of alkyl groups containing from about 10 to about 22 carbon atoms, preferably from about 12 to about 18 carbon atoms, alkyl aryl and aryl alkyl groups containing a similar number of carbon atoms with a benzene ring being treated as equivalent to about 2 carbon atoms, and similar structures interrupted by amido or ether linkages; each $R_1$ is an alkyl group containing from 1 to about 3 carbon atoms; and $R_2$ is an alkylene group containing from 1 to about 6 carbon atoms.

Examples of preferred betaines are dodecyl dimethyl betaine, cetyl dimethyl betaine, dodecyl amidopropyldimethyl betaine, tetradecyldimethyl betaine, tetradecylamidopropyldimethyl betaine, and dodecyldimethylammonium hexanoate.

Useful fatty acid amides include those which are known to the art. Particular exemplary fatty acid amide surfactants include ammonia, monoethanol, and diethanol amides of fatty acids having an acyl moiety which contains from about 8 to about 18 carbon atoms, and which may be represented in accordance with the formula:

$$R_1-CO-N(H)_{m-1}(R_2OH)_{3-m}$$

where $R_1$ represents a saturated or unsaturated aliphatic hydrocarbon radical of from about 7 to 21 carbon atoms, but preferably from about 11 to 17 carbon atoms; $R_2$ represents a $-CH_2-$ or $-CH_2CH_2-$, and m is an integer from 1 to 3, but is preferably 1. Preferably, $R_1$ is a saturated or unsaturated aliphatic hydrocarbon radical comprising from about 11 to 17 carbon atoms, and m is 1.

Further examples of such compounds include monoethanol amine coconut fatty acid amide and diethanol amine dodecyl fatty acid amide. An exemplary useful fatty acid amide includes cocomonoethanol amide or cocodiethanolamide, which are presently commercially available as MONAMID(RTM) CMA (Mona Industries, Paterson N.J. (USA)).

What is to be understood by the term "concentrate" and "concentrate composition" in this specification and claims is the pre-consumer dilution and composition of the cleaning composition which is the essentially the form of the product prepared for sale to the consumer or other, end user. Similarly, what is to be understood by the term "cleaning compositions" are the water diluted compositions which are expected to be prepared by the consumer or other end user by mixing a measured amount of the "concentrate" with water in order to form an appropriately diluted cleaning composition which is suitable for use in cleaning applications, especially in the cleaning of hard surfaces.

It is also to be understood, that proportions of one or more constituents have been and generally are referred to as percent by weight or as parts by weight based on a measure of 100% by weight, unless otherwise indicated.

According to certain particularly preferred embodiments of the invention there are provided object of the invention to provide an aqueous concentrated liquid hard surface cleaning composition which blooms when added to a larger volume of water which comprises the following constituents:

0.1–35% wt. of an organic solvent constituent;
0.5–10% wt. of a germicidal constituent which provides a primary sanitizing benefit, preferably a quaternary ammonium compound;
0.2–10% wt. of a binary co-solvent system comprising an alkyl diphenyl solvent and a co-solvent;
0.1–10% wt. of at least one further detersive surfactant constituent;
0–20% wt. of at least one optional constituent selected from: chelating agents, coloring agent, light stabilizers, fragrances, thickening agents, hydrotropes, pH adjusting agents, pH buffers Certain particularly preferred embodiments of the invention, as well as certain particularly preferred constituents and particularly preferred weight ranges are demonstrated in the Examples shown described on Table 1, below.

As generally denoted above, the formulations according to the invention include both cleaning compositions and concentrates as outlined above which differ only in the relative proportion of water to that of the other constituents forming such formulations. As noted, the concentrate may be used without dilution, i.e., in concentrate:water concentrations of 1:0, to extremely dilute dilutions such as 1:10,000. Desirably, the concentrate is diluted in the range of 1:0.1–1:1000, preferably in the range of 1:1–1:500 but most preferably in the range of 1:10–1:100. Generally better cleaning results are to be expected at lower relative dilutions of the concentrate in water.

In accordance with preferred embodiments of the invention, when a quantity of the concentrate compositions taught herein are added to a larger volume of water, a blooming characteristic is manifested. Such "blooming" may be broadly characterized as the formation of milky, creamy or cloudy appearance which is manifested when a dilutable composition is added to a larger volume or quantity of water. Such "blooming" may be alternately characterized as the reduction of transmitted light through an amount of water by at least 30%, desirably by at least 40%, yet more desirably by at least about 50%, and yet most desirably by at least 60% or more when a dilution of the concentrate composition:water with the weight or volume ratio range of from 1:64 to 1:102, especially at a 1:64 is formed. That such blooming may be attained without the use of pine oil fractions as is common in certain commercially available pine oil containing preparations is surprising.

Such dilution ratios of concentrate:water as described above may be volume/volume basis, or a weight/weight basis.

As has been noted, concentrate compositions according to preferred embodiments of the invention exhibit a long lasting blooming effect when they are diluted into a larger volume of water, especially when used to form (weight ratio) dilutions with water of concentrate:water of 1:64 at room temperature. Desirably, such dilutions do not exhibit an increase in light transmittance in accordance with the measurement methods discussed in the Examples below, of more than 50% (based on the initial 'as mixed' value) during its initial three-day interval.

The concentrate compositions according to the invention, and aqueous dilutions formed therefrom, are particularly useful in the cleaning of hard surfaces. Hard surfaces which are to be particularly denoted include those associated with Kitchen environments, lavatory environments, especially flooring surfaces and the surfaces of fixtures (doors, cabinets, shelving, and the like) in such environments.

EXAMPLES

A number of formulations were produced by mixing the constituents outlined in Table 1 by adding the individual constituents into a beaker of deionized water at room temperature which was stirred with a conventional magnetic stirring rod. The order of addition is not critical, but good results are obtained where the surfactants are added to the water prior to Stirring continued until the formulation was homogenous in appearance. It is to be noted that the constituents might be added in any order, but it is preferred that water be the initial constituent provided to a mixing vessel or apparatus as it is the major constituent and addition of the further constituents thereto is convenient. The exact compositions of the example formulations are listed on Table 1, below.

TABLE 1

|  | Ex.1 | Ex.2 | Ex.3 | Ex.4 | Ex.5 |
|---|---|---|---|---|---|
| EMCOL(RTM) CNP-110 | — | — | 0.5 | — | — |
| TOMAH(RTM) AO-728 special (50%) | — | — | — | — | 0.5 |
| TRITON(RTM) 15-S-9 | — | — | — | 0.5 | — |
| PLURONIC(RTM) L-64 | — | — | — | — | — |
| GLUCOPON(RTM) 425N (50%) | — | — | — | — | — |
| quaternary ammonium chloride | 5.0 | 5.0 | 5.0 | 5.0 | 5.0 |
| isopropyl alcohol | 12 | 12 | 12 | 12 | 12 |
| lauryl alcohol | 4.55 | 4.5 | 4.5 | 4.5 | 4.5 |
| propylene glycol | 20 | 20 | 20 | 20 | 20 |
| diphenyl solvent | 4.0 | 3.5 | 3.5 | 3.5 | 3.5 |
| Na$_2$EDTA | 0.5 | 0.5 | 0.5 | 0.5 | 0.5 |
| di water | q.s. | q.s. | q.s. | q.s. | q.s. |

|  | Ex.6 | Ex.7 | Ex.8 |
|---|---|---|---|
| EMCOL(RTM) CNP-110 | — | — | — |
| TOMAH AO-728(RTM) special (50%) | — | — | — |
| TRITON(RTM) 15-S-9 | — | — | — |
| PLURONIC(RTM) L-64 | 0.5 | — | — |
| GLUCOPON(RTM) 425N (50%) | — | 1.0 | — |
| quaternary ammonium chloride | 5.0 | 5.0 | 5.0 |
| isopropyl alcohol | 12 | 12 | 12 |
| lauryl alcohol | 4.5 | 4.5 | 3.55 |
| propylene glycol | 20 | 20 | 20 |
| diphenyl solvent | 3.5 | 3.5 | 3.0 |
| Na$_2$EDTA | 0.5 | 0.5 | 0.5 |
| di water | q.s | q.s. | q.s. |

All of the formulations on Table 1 indicated in weight percent, and the percent actives of individual constituents are 100% unless otherwise indicated.

The identity of the constituents indicated on Table 1 are indicated on the following table.

TABLE 2

| EMCOL (RTM) CNP-110 | alkylpolycarboxylate, nonionic surfactant (100% wt. actives) from Witco Chem. Co. |
|---|---|
| TOMAH (RTM) AO-728 special (50%) | bis-(2-hydroxyethyl $C_{12}$–$C_{15}$ alkyloxypropyl) amine oxide (50% wt. actives) Tomah Products Co. |
| TRITON (RTM) 15-S-9 | $C_{11}$–$C_{15}$ secondary alkyl ethoxylate, with an average of 9 moles of ethylene oxide (100% wt. active) from Union Carbide Corp. |
| PLURONIC (RTM) L64 | a block copolymer of ethylene oxide/propylene oxide (100% wt. actives) from BASF Inc. |
| GLUCOPON (RTM) 425N (50%) | technical grade mixture of $C_8$, $C_{10}$, $C_{12}$, $C_{14}$ and $C_{16}$ alkylpolyglucosides, nonionic surfactant (50% wt. active) from Henkel Corp. |
| quaternary ammonium chloride | technical grade mixture of n-alkyl dimethyl benzyl ammonium chloride having 50% of $C_{14}$, 40% of $C_{12}$ and 10% $C_{16}$ alkyl distribution (80% wt. active) as BTC-8358 from Stepan Inc. |
| isopropyl alcohol | propan-2-ol from Eastman Chemical Co. (100% wt. active) |
| lauryl alcohol | technical grade mixture of 65–75% wt. of 1-dodecanol, 22–28% wt. 1-tetradecanol, 4–8% wt. 1-hexadecanol and 0–0.5% 1-decanol (totaling 100% wt. active) as Henkel 3333 LOROL (RTM) C12–14A |
| propylene glycol | 1,2-propane diol, from Eastman Chemical Co. (100% wt. active) |
| diphenyl solvent | technical grade mixture of alkyl diphenyls (100% wt. actives) as NUSOLV (RTM) ABP-103 from Arristec Inc. |
| Na$_2$EDTA | disodium salt of ethylenediaminetetraacetic acid (100% wt. actives) |
| di water | deionized water |

The blooming characteristics of these formulations was characterized by using the BRINKMAN SYBRON (RTM) PC 801 colorimeter. Each tested formulation were diluted with tap water in a weight ratio of 1:64, and the test was carried out with each of the formulations and water at room temperature (680° F., 20° C.). The resulting determined values, reported as "blooming" in the following table provide an empirical evaluation in percent transmittance (%) of the degree of transparency of a diluted example formulation wherein 0% indicates complete opacity and 100% the transparency of a tap water sample. The result was tabulated as follows:

TABLE 3

| | % Transmittance |
|---|---|
| DETTOL (RTM) | 0.5 |
| Ex.1 | 0.7 |
| Ex.2 | 0.5 |
| Ex.3 | 0.4 |
| Ex.4 | 0.6 |
| Ex.5 | 0.7 |
| Ex.6 | 1.2 |
| Ex.7 | 1.3 |
| Ex.8 | 5.0 |

As a comparative example, a comparison was made using a sample of DETTOL(RTM), (ex. Reckitt & Colman, p.l.c., England) a soap based cleaning and disinfecting composition known to provide a particularly substantive "bloom". This sample was tested as per the formulations according to the present invention. As can be seen from the results of Table 3, the formulations according to the invention provided a very substantive "bloom" which was in many cases comparable to that provided by the DETTOL(RTM) sample.

Cleaning Test

Cleaning efficacy was measured for weight ratios of 1:64 (concentrate composition:water) aqueous dilutions of formulations according to Ex. 2 and as a control composition, as described above. The test was carried out using the ASTM D4488-89, Annex A2 method—greasy soil on painted masonite wallboard test, using a Gardner Washability Apparatus.

Latex painted masonite wallboard is soiled with a mixture of melted, oily soils containing a small amount of carbon black and allowed to set overnight. A first aqueous dilution is applied to a sponge that scrubs half the soiled substrate in a straight-line using the Gardner Washability Apparatus. Afterwards, the second aqueous dilution is applied to a further sponge that scrubs the other half of the soiled substrate in a similar manner.

In determining the cleaning efficiency, reflectance values were determined using a Gardner Lab Scan Reflectometer for each of the following: a clean unsoiled panel, a soiled panel, and a soiled panel following Gardner Washability Apparatus scrubbing. Such reflectance values were then employed to calculate % cleaning efficiency according to the following formula:

$$\% \text{ Cleaning Efficiency} = \frac{Lt - Ls}{Lo - Ls} \times 100\%$$

wherein,
Lt=% reflectance average after scrubbing solid tile
Ls=% reflectance average before cleaning soiled tile
Lo =% reflectance average original tile before soiling Cleaning efficiency results for Formulation 1 are shown in Table 4, hereinafter.

TABLE 4

| | % Cleaning Efficacy |
|---|---|
| DETTOL (RTM) | 59.7 |
| Ex. 7 | 60.2 |
| Ex. 8 | 54.7 |

As shown, the measurement of the cleaning effectiveness of the test samples involved the ability of the cleaning composition to remove the test soil from the test substrate. This was expressed by % Cleaning Efficiency. As numerical values for a % Cleaning Efficiency increase, higher cleaning effectiveness is achieved for the cleaning composition tested. As the results show, the inventive composition showed an excellent cleaning property.

Evaluation of Antimicrobial Efficacy

Ex. 2 (diluted 1 part to 64 parts water) was evaluated for antimicrobial activity using the Biomek(RTM) 2000 Laboratory Automation Workstation together with the BioWorks (RTM) Operating System (available from Beckman Coulter Inc., Fullerton, Cailf.). The organism tested was *Staphylococcus aureus* at a concentration of 9 logs. The biomek simulates a microbial reduction suspension test. One part of organism suspension (*Staphylococcus aureus*) is added to 9 parts of E1 in an appropriate container. Deonized water (DI $H_2O$) was used as a control. The organism and sample are then mixed thoroughly for 15 seconds. Serial tenfold dilutions are carried out in a neutralizing broth. The diluted samples are then incubated for 24–48 hours at 35–37° C. Thereafter, surviving organisms are quantified and log reduction, as a measurement of organism survivors are calculated as follows:

Log Reduction=(Log Survivors/deionized $H_2O$)–(Log Survivors/Sample)

Ex. 2 had a log reduction of 6.7.

As may, be seen from the results indicated above, the compositions according to the invention provide excellent cleaning benefits to hard surfaces, including hard surfaces with difficult to remove stains notwithstanding the low solids content of the inventive compositions. These advantages are further supplemented by the excellent antimicrobial efficacy of these compositions against known bacteria commonly found in bathroom, kitchen and other such advantages clearly illustrate the superior characteristics of the compositions, the cleaning and antimicrobial benefits attending its use which is not before known to the art.

What is claimed is:

1. An aqueous concentrated liquid hard surface cleaning composition which blooms when added to larger volume of water, said composition comprising:
   an organic solvent constituent;
   a germicidal constituent which provides a primary sanitizing benefit; and
   a binary co-solvent system comprising an alkyl diphenyl solvent and at least one co-solvent,
   which composition is essentially free of terpene solvents.

2. A cleaning composition according to claim 1 wherein the germicidal constituent is a quaternary ammonium compound.

3. A cleaning composition according to claim 2 wherein the alkyl diphenyl solvent is a compound of the formula

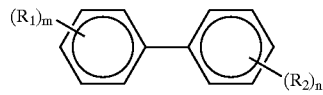

wherein
   $R_1$ is hydrogen or a $C_1$–$C_{10}$ lower alkyl radical,
   $R_2$ is hydrogen or a $C_1$–$C_{10}$ lower alkyl radical,
   m is an integer from 1 to 3, and
   n is an integer from 1 to 3.

4. A cleaning composition according to claim 3 wherein
   $R_1$ is hydrogen or a $C_1$–$C_6$ straight chain or branched alkyl radical, and
   $R_2$ is a $C_1$–$C_6$ straight chain or branched alkyl radical.

5. A cleaning composition according to claim 4 wherein $R_1$ is a $C_1$–$C_6$ straight chained or branched alkyl radical.

6. A cleaning composition according to claim 4 wherein:
   $R_1$ is hydrogen, and
   m is 1.

7. A cleaning composition according to claim 2 wherein the organic solvent constituent is selected from the group consisting of water-miscible alcohols, ethers, glycol ethers, lower esters of monoalkyl ethers of ethylene glycol or propylene glycol, and mixtures thereof.

8. A cleaning compositions according to claim 7 wherein the organic solvent constituent comprises propylene glycol.

9. A cleaning composition according to claim 7 wherein the organic solvent constituent comprises a glycol ether of the formula

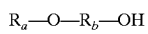

wherein
   $R_a$ is a $C_1$–$C_{20}$ alkyl radical or an aryl of at least 6 carbon atoms, and
   $R_b$ is a $C_1$–$C_8$ alkylene radical or is an ether or polyether having from 2 to 20 carbon atoms.

10. A cleaning composition according to claim 9 wherein the organic solvent constituent comprises propylene glycol methyl ether, dipropylene glycol methyl ether, tripropylene glycol methyl ether, propylene glycol isobutyl ether, ethylene glycol methyl ether, ethylene glycol ethyl ether, ethylene glycol butyl ether, diethylene glycol phenyl ether or propylene glycol phenol ether.

11. A cleaning composition according to claim 10 wherein the organic solvent constituent is ethylene glycol n-butyl ether, diethylene glycol n-butyl ether or a mixture thereof.

12. A cleaning composition according to claim 7 wherein the organic solvent constituent comprises a monohydric $C_1$–$C_6$ primary or secondary alcohol.

13. A cleaning composition according to claim 12 wherein the organic solvent constituent is isopropanol.

14. A cleaning composition according to claim 3 wherein the co-solvent comprises one or more monohydric $C_8$–$C_{18}$ primary alcohols.

15. A cleaning composition according to claim 14 in which the co-solvent is lauryl alcohol, myristyl alcohol, cetyl alcohol or mixtures thereof.

16. A cleaning composition according to claim 15 in which the co-solvent is lauryl alcohol.

17. A cleaning composition according to claim 2 which comprises one or more quaternary ammonium germicides of the formula:

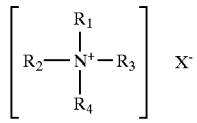

wherein
   at least one of $R_1$, $R_2$, $R_3$ and $R_4$ is a hydrophobic, aliphatic aryl aliphatic or aliphatic aryl radical of from 6 to 26 carbon atoms,
   the entire cation portion of the molecule has a molecular weight of at least 165, and
   X is salt-forming anionic radical.

18. A cleaning composition according to claim 17 wherein the quaternary ammonium germicide is of the formula:

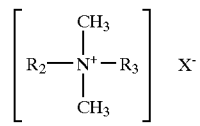

wherein
   $R_2$ and $R_3$ are the same or different $C_8$–$C_{12}$ radicals,
   or $R_2$ is $C_{12-16}$ alkyl, $C_{8-18}$ alkylethoxy, $C_{8-18}$ alkylphenolethoxy and $R_3$ is benzyl, and
   X is a halide or methosulfate.

19. A cleaning composition according to claim 18 wherein the alkyl groups are straight-chained and X is chloride.

20. A cleaning composition according to claim 2 which additionally comprises a further detersive surfactant constituent selected from the group consisting of nonionic anionic and amphoteric surfactants and mixtures thereof.

21. A cleaning composition according to claim 20 in which the further detersive surfactant constituent comprises an alkyl ether carboxylate.

22. A cleaning composition according to claim 20 in which the further detersive surfactant constituent comprises an ethylene oxide/propylene oxide surfactant.

23. A cleaning composition according to claim 20 in which the further detersive surfactant constituent comprises an alcohol ethoxylate.

24. A cleaning composition according to claim 20 in which the further detersive surfactant constituent comprises an amine oxide.

25. A cleaning composition according to claim 20 which the further detersive surfactant constituent comprises an alkylpolyglucoside.

26. A cleaning composition according to claim 2 which includes one or more additional constituents selected from the group consisting of chelating agents, coloring agents, light stabilizers, fragrances, thickening agents, hydrotropes, pH adjusting agents and pH buffers.

27. An aqueous concentrated liquid hard surface cleaning composition which comprises:
   0.1–35% wt. of an organic solvent constituent;
   0.5–10% wt. of a germicidal constituent which provides a primary sanitizing benefit,
   0.2–10% wt. of a binary co-solvent system comprising an alkyl diphenyl solvent and a co-solvent;
   0.1–10% wt. of at least one further detersive surfactant constituent; and
   0–20% wt. of at least one optional constituent selected from the group consisting of chelating agents, coloring agents, light stabilizers, fragrances, thickening agents, hydrotropes, pH adjusting agents and pH buffers.

28. A cleaning composition according to claim 27 wherein the germicidal constituent is a quaternary ammonium compound.

29. A cleaning composition according to claim 27 which blooms when diluted at a 1:64 v/v ratio in room temperature water.

30. A method for cleaning a hard surface which comprises the step of contacting the hard surface with an aqueous liquid hard surface cleaning composition comprising
   0.1–35% wt. of an organic solvent constituent;
   0.5–10% wt. of a germicidal quaternary ammonium constituent 0.2–10% wt. of a binary co-solvent system comprising an alkyl diphenyl solvent and a co-solvent;

0.1–10% wt. of at least one further detersive surfactant constituent;

0–20% wt. of at least one optional constituent selected from the group consisting of chelating agents, coloring agents, light stabilizers, fragrances, thickening agents, hydrotropes, pH adjusting agents and pH buffers, said composition being diluted to a ratio of from 1:64 to 1:102.

* * * * *